United States Patent
Siedenburg et al.

(10) Patent No.: US 10,117,642 B2
(45) Date of Patent: Nov. 6, 2018

(54) ULTRASOUND TRANSDUCER WITH SEALED, ACTIVE COOLING

(71) Applicant: FUJIFILM SonoSite, Inc., Bothell, WA (US)

(72) Inventors: Clinton T. Siedenburg, Everett, WA (US); John R. Stice, Seattle, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 210 days.

(21) Appl. No.: 14/630,609

(22) Filed: Feb. 24, 2015

(65) Prior Publication Data

US 2016/0242747 A1    Aug. 25, 2016

(51) Int. Cl.
*A61B 8/00* (2006.01)
*G01S 7/52* (2006.01)

(52) U.S. Cl.
CPC ............ *A61B 8/546* (2013.01); *A61B 8/4444* (2013.01); *G01S 7/5208* (2013.01); *A61B 8/4472* (2013.01)

(58) Field of Classification Search
CPC ..... A61B 8/4444; A61B 8/4472; A61B 8/546; G01S 7/5208
See application file for complete search history.

(56) References Cited

U.S. PATENT DOCUMENTS

| | | | | |
|---|---|---|---|---|
| 2,830,165 A * | 4/1958 | Carlin | ................. | B06B 1/08 228/118 |
| 3,100,853 A * | 8/1963 | Kleesattel | ............. | B01D 41/04 310/26 |
| 3,321,871 A * | 5/1967 | Balamuth | ............... | B24B 53/00 451/28 |
| 4,164,690 A * | 8/1979 | Muller | ................ | F04D 25/0653 310/63 |
| 4,757,716 A * | 7/1988 | Nottingham | .......... | F01D 21/003 73/623 |
| 4,893,815 A * | 1/1990 | Rowan | .................... | F41B 15/04 42/1.08 |
| 4,951,677 A * | 8/1990 | Crowley | .............. | A61B 5/6848 600/109 |
| 5,178,150 A * | 1/1993 | Silverstein | ............. | A61B 1/018 600/446 |
| 5,560,362 A * | 10/1996 | Sliwa, Jr. | ............... | A61B 8/546 600/439 |
| 5,993,378 A * | 11/1999 | Lemelson | .......... | A61B 1/00096 600/109 |
| 6,360,027 B1 * | 3/2002 | Hossack | ................ | A61B 8/145 348/384.1 |

(Continued)

*Primary Examiner* — Philip R Wiest
*Assistant Examiner* — Guy K Townsend
(74) *Attorney, Agent, or Firm* — Perkins Coie LLP

(57) ABSTRACT

A scan head for an ultrasound imaging device has a body that encloses a number of ultrasound transducers and controlling electronics. The electronics are sealed in the body of the scan head. The scan head has a fan that is configured to remove heat caused by the operation of the electronics. The motor is magnetically controlled and has controlling electronics that are sealed in the body of the scan head. In one embodiment, an airflow channel surrounds the electronics in the scan head and the fan is configured to move air through the airflow channel. In another embodiment, the electronics are thermally coupled to a heat exchanger heat via a conductive substrate and the fan is configured to move air over the heat exchanger.

3 Claims, 3 Drawing Sheets

(56) References Cited

U.S. PATENT DOCUMENTS

| | | | | |
|---|---|---|---|---|
| 7,604,965 | B2* | 10/2009 | McBride | C12Q 1/68 |
| | | | | 435/91.2 |
| 8,133,178 | B2* | 3/2012 | Brauker | A61B 5/1411 |
| | | | | 600/365 |
| 8,162,606 | B2* | 4/2012 | Jolly | B64C 27/001 |
| | | | | 416/1 |
| 8,267,652 | B2* | 9/2012 | Jolly | B64C 27/001 |
| | | | | 415/1 |
| 8,434,160 | B1* | 4/2013 | Adams | G01N 29/036 |
| | | | | 850/56 |
| 2002/0095087 | A1* | 7/2002 | Mourad | A61B 5/0048 |
| | | | | 600/442 |
| 2002/0135255 | A1* | 9/2002 | Willliams | F04D 25/08 |
| | | | | 310/166 |
| 2003/0157070 | A1* | 8/2003 | Jolly | C07K 14/005 |
| | | | | 424/93.21 |
| 2004/0004559 | A1* | 1/2004 | Rast | G02B 27/017 |
| | | | | 341/34 |
| 2009/0148342 | A1* | 6/2009 | Bromberg | A01N 59/00 |
| | | | | 422/37 |
| 2010/0022882 | A1* | 1/2010 | Duckworth | A61B 5/6805 |
| | | | | 600/447 |
| 2010/0081893 | A1* | 4/2010 | Jarvik | A61B 5/4824 |
| | | | | 600/301 |
| 2013/0261368 | A1* | 10/2013 | Schwartz | A61N 5/1027 |
| | | | | 600/1 |
| 2015/0141975 | A1* | 5/2015 | Bangera | A61M 35/00 |
| | | | | 606/21 |

* cited by examiner

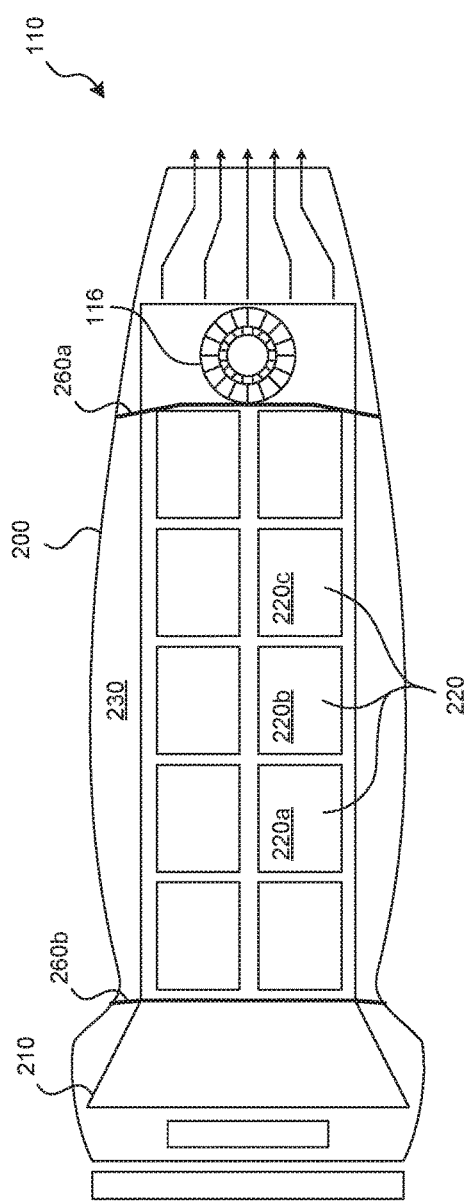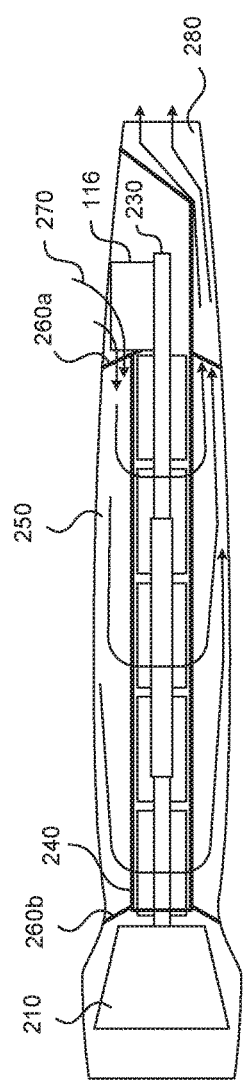
FIG. 2
FIG. 3

ULTRASOUND TRANSDUCER WITH SEALED, ACTIVE COOLING

TECHNICAL FIELD

The technology disclosed relates to medical imaging systems in general and to ultrasound imaging systems in particular.

BACKGROUND

Ultrasound is a commonly used, non-invasive technique for imaging internal body tissues of subjects. To produce an image, high frequency acoustic signals are transmitted into the body and corresponding echo signals are received and analyzed. The echo signals are analyzed for such factors as amplitude, delay, Doppler shift etc. The analyzed signals are then used to produce images of the tissue under examination.

Despite advances in the signal processing power of electronics and integrated circuit miniaturization, portable ultrasound systems generally lack the signal processing capabilities of cart-based systems. One reason for this is heat generation. The electronics that drive the ultrasonic transducers and analyze the received echo signals generate significant amounts of heat. While heat generation is easily handed in larger systems that can include fans and/or liquid cooling systems, these cooling systems are generally too bulky to fit in more portable systems or are not compatible with cleaning regimens. Therefore, most portable systems are either simpler systems that don't produce as much heat or systems that divide the signal processing functions among several components so that no one component exceeds safety guidelines for heat generation when used. Dividing the signal processing functions among different components can lessen the amount of heat that each component generates. However, the wires or other mechanisms for transmitting signals between the components to do the signal processing can be a significant source of noise or other parasitic effects.

Given these problems, there is a need for a mechanism that allows greater amounts of signal processing to be performed in a portable ultrasound imaging system and can dissipate greater amounts of heat.

SUMMARY

As will be described in further detail below, the disclosed technology relates to ultrasound imaging systems and in particular to an ultrasound scan head that includes an array of ultrasound transducer elements and processing electronics. In one embodiment, such processing electronics includes transmit receive (TX/RX) circuitry, beamforming circuitry and scan conversion circuitry. The scan head is connected to a display unit via a wired or wireless communication link. Ultrasound signals that are processed in the scan head are transmitted to the display unit for a user to view.

In one embodiment, the scan head includes a fan that circulates air within an air passage that surrounds a sealed chamber in which the processing electronics are located. The fan is preferably a magnetic induction type whereby the electronics and drive coils that control the fan are sealed in the scan head while a rotor with a number of fan blades is exposed to the air. The rotor can be removed from the scan head for cleaning. Alternatively, because the electronics in the scan head are sealed, the body of the scan head can be immersed in a cleaning solution and the fan operated to flush the cleaning solution though the air passage that surrounds the electronics.

In another embodiment, the processing electronics in the scan head are thermally coupled to a heat sink through a heat conductive conduit. A fan in the scan head operates to move air over or through the heat sink to remove heat from the scan head. The fan is preferably a magnetic induction type whereby the electronics and drive coils that control the fan are sealed in the scan head while a rotor having fan blades that move the air over or through the heat exchanger, is exposed to the air.

BRIEF DESCRIPTION OF THE DRAWINGS

FIG. 2 shows a scan head having electronics that are within a sealed enclosure and a fan for cooling the electronics in accordance with an embodiment of the disclosed technology;

FIG. 3 shows an airflow path through a scan head in accordance with an embodiment of the disclosed technology;

DETAILED DESCRIPTION

Figure 1:
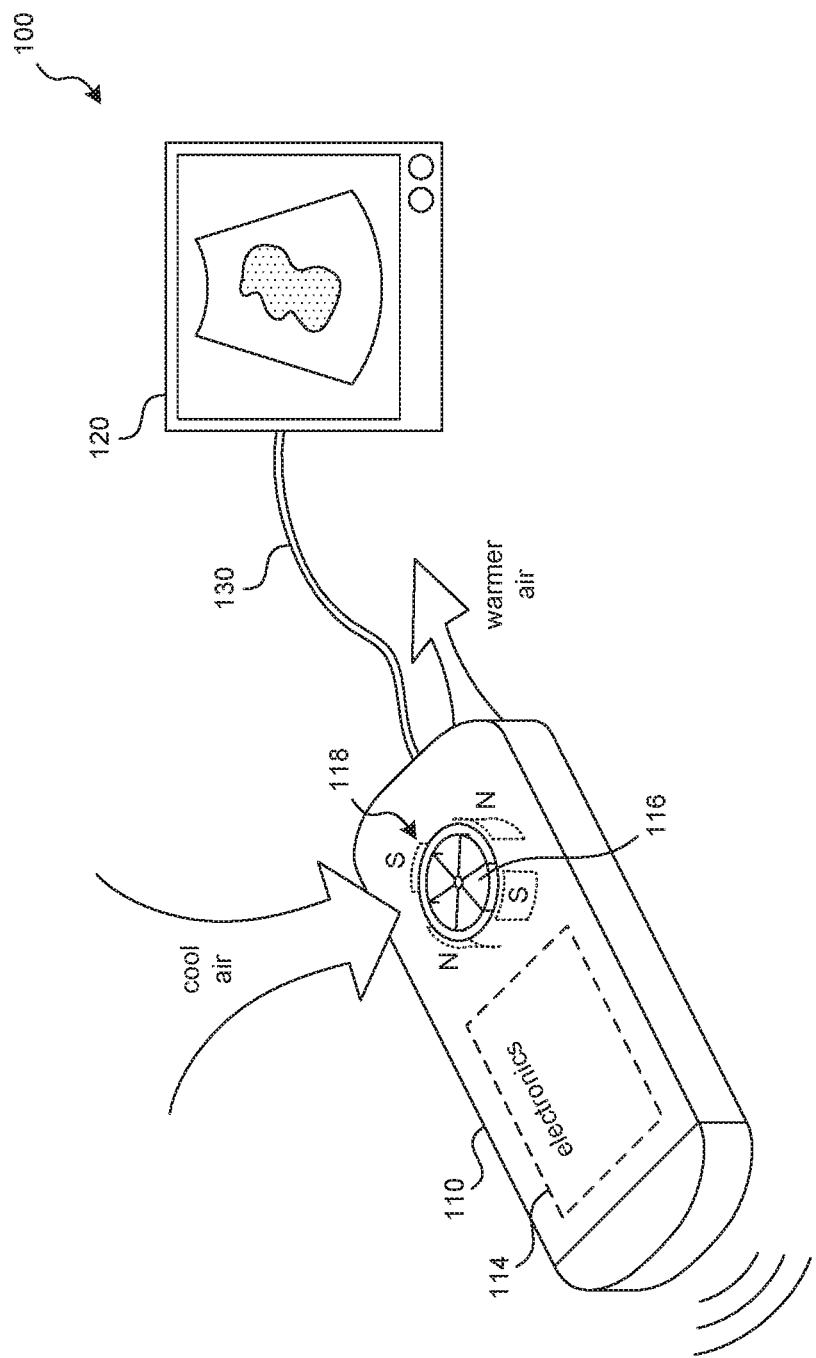
FIG. 1 shows an ultrasound imaging system in accordance with one embodiment of the disclosed technology.

FIG. 1 shows an illustration of a portable ultrasound imaging system constructed in accordance with an embodiment of the disclosed technology. The ultrasound imaging system 100 includes a scan head 110 and a display device 120. The scan head 110 is configured to direct ultrasound energy towards an object of interest and to receive corresponding echo signals. The scan head includes an array of transducer elements and electronics 114 to generate the ultrasound pulses for transmission and to receive the corresponding echo signals. In addition, the electronics convert the received echo signals from an analog to a digital form and beamform the digital signals by combining signals from different transducer elements with the appropriate weights and delays in order to detect echo signals produced from a particular depth and direction. Furthermore, the electronics may convert the beamformed echo signals into a format that is ready for display on the display device. Signals produced in the scan head 110 are sent to the display device 120 via a wired or wireless communication link 130 so that a user can view an image of the object of interest. The particular functions that are performed by the electronics in the scan head may vary depending on the size of the electronic components and the level of integration desired.

As discussed above, the amount of signal processing functions that can be performed by electronics in the scan head 110 may be limited by heat generated during operation. There are FDA guidelines regarding how hot a handheld medical device can become during operation for patient safety. To address this problem, a scan head constructed in accordance with an embodiment of the disclosed technology includes an active cooling mechanism to remove heat that is generated during operation. In the embodiment shown, the active cooling mechanism is a fan 116 having blades that pull in cooler air to remove heat from the electronics. The fan 116 is controlled by motor control electronics 118 that are sealed within the body of the scan head 110. In one embodiment, the fan 116 is a magnetic induction type that responds to alternating magnetic fields to move the fan blades. Because the motor control electronics 118 are sealed within the scan head, the scan head can be easily cleaned.

As shown in FIGS. 2 and 3, one embodiment of the scan head 110 constructed in accordance with the disclosed technology includes an outer shell 200 having an ergonomic shape that can be held in the operator's hand. A distal end of the scan head has an array of transducer elements 210 that produce high frequency acoustic signals and direct them into the object of interest as well as receive the corresponding echo signals. Electrically connected to the transducer elements 210 are a number of electronic components 220a, 220b, 220c etc. comprising one or more of individual components, integrated circuits, ASICs, digital signal processors (DSPs) as well as power conditioning circuitry and the like that operate to drive the transducer elements and process the received echo signals. In one embodiment, the electronic components 220 are mounted to a thermally conductive substrate 230, such as a thermally conductive printed circuit board, that draws the heat created by the components during operation. In one embodiment, the electronic components 220 and their connections to the transducer elements 210 are contained within a sealed compartment 240 having an outer surface that is spaced apart from the inner surface of the outer shell 200 such that there is an air gap or plenum formed between the sealed compartment 240 and the inside of the outer shell. The sealed compartment 240 can be made of a heat conductive plastic, metallic coated plastic, metal or other material that allows it to both radiate heat from the thermally conductive substrate 230 and be hermetically sealed. Metallic coated plastic compartments or metal enclosures have the additional advantage of providing electrical interference shielding to the electronic components inside the sealed compartment.

As best shown in FIG. 3, the sealed compartment 240 is supported within the outer shell 200 by a pair of environmental barriers 260a and 260b towards the proximal and distal ends of the scan head 110 respectively. In one embodiment, the environmental barriers support the conductive substrate 230 within the hollow portion of the shell 200 so that an air gap or plenum 250 is formed around the outside of the sealed compartment 240 and inside of the outer shell 200. In one embodiment, the distal barrier 260b seals the distal end of the scan head so that liquids or other materials encountered during use of the scan head or during cleaning do not enter the transducer elements' 210 enclosure. The proximal environmental barrier 260a has one or more openings in it so that air can pass through the openings in order to remove heat from the scan head.

As best shown in FIG. 3, the sealed compartment 240 extends through the environmental barrier 260a to the proximal end of the scan head in order to divide the interior of the shell into a top half and a bottom half. An airflow entrance 270 on the top half is physically separated from an air flow exit 280 on the bottom half of the scan head.

In the embodiment shown, the scan head includes the fan 116 that is supported on the conductive substrate 230. The fan 116 is preferably a magnetic induction type where the controlling electronics and magnetic field generators are sealed in the sealed compartment 240. The fan 116 includes a rotor that supports a number of fan blades that interact with the magnetic fields produced by the motor control electronics in order to spin and drive air from outside the scan head and through the air gaps in the environmental barrier 260a. As the fan is rotating, cooler air enters the airflow entrance 270, is pushed through the plenum 250 where it is warmed by the heat produced by the electronics 220 in the sealed compartment 240 and exits the scan head at the airflow exit 280.

In one embodiment, the rotor on the fan is held in place by magnetic forces and can be removed from the scan head for cleaning. In one embodiment, the rotor includes a central spindle made of a ferromagnetic material that fits within a sealed hole on the conductive substrate and is held in place with a magnetic force. Alternatively, the spindle can be held in place with a friction fit. Because the rotor is removable from the body of the scan head, the scan head can be cleaned with antiseptic cleaning solutions. Preferably the opening in the body of the scan head in which the rotor fits is relatively smooth or otherwise free of cracks and crevices that may make cleaning difficult. Once removed, the rotor of the fan 116 can be subjected to alternative methods of cleaning (heat, chemical, mechanical or the like) that can clean the various surfaces of the fan blades.

Alternatively, because the scan head electronics and motor control electronics are hermitically sealed in the sealed compartment 240, the entire scan head can be immersed in a cleaning liquid. The rotor can be operated by the controlling electronics to rotate either in one direction or back and forth to move the cleaning fluid through the plenum 250.

In one embodiment, processed echo signals are sent to the display unit 120 via a wireless or wired (not shown) connection. The wired connection preferably terminates in the sealed compartment 240 so that the scan head can be immersed if desired without shorting the contacts in the wired connection.

In another embodiment, the scan head 110 does not include an air gap or plenum through which cooling air is directed to remove heat from the scan head. In an embodiment shown in FIGS. 4 and 5, a scan head 400 has a proximal end and a distal end. At the distal end are a number of transducer elements 420 that are electrically coupled to a number of electronic components 430a, 430b, and 430c etc. The electronic components 430 are mounted on a heat conductive substrate 440 that operates to direct heat to a heat exchanger or heat sink 450 that is located toward the proximal end of the substrate 440. The heat exchanger may include a number of channels or fins to aid in heat dissipation. Alternatively, the heat exchanger may include only smooth surfaces of metal or other heat conductive material to aid in cleaning.

An environmental barrier 460 hermetically seals the electronics within the scan head. A portion of the substrate extends through the environmental barrier 460 and supports the heat exchanger 450. The fan 116 is positioned on the other side of the conductive substrate 440 and has controlling electronics and coils (not shown) that are sealed within the scan head. The fan 116 includes a removable rotor with fan blades that are driven by the magnetic fields produced by the controlling electronics to move air through or over the heat exchanger 450. In the embodiment shown, the warmed air from the heat exchanger exits the scan head at an exhaust port 480 that is located at the proximal end of the scan head.

Figure 5:
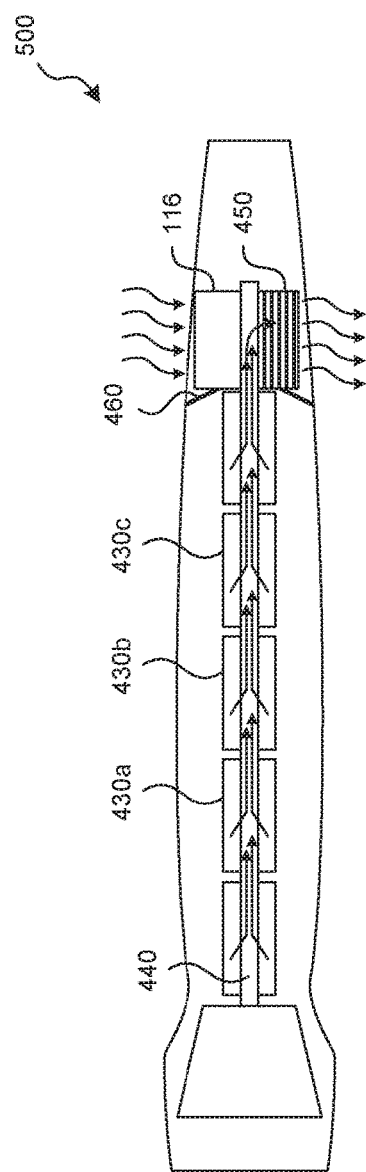
FIG. 5 shows an airflow path created by a fan in the scan head to remove heat from the heat exchanger in accordance with an embodiment of the disclosed technology.

In the embodiment shown in FIG. 5, the exhaust port 480 is omitted and the warmed air from the heat exchanger 450 is vented out one side 500 of the scan head.

Figure 4:
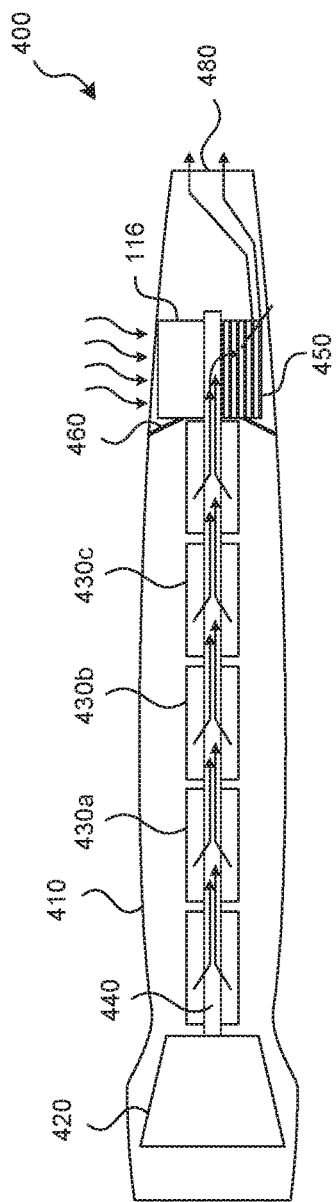
FIG. 4 shows a scan head having electronics that are sealed in the scan head and thermally coupled to a heat exchanger in accordance with another embodiment of the disclosed technology.

In both embodiments shown in FIGS. 4 and 5, the controlling electronics for the fan 116 are sealed inside the scan head but the rotor is removable for cleaning. Alternatively, the entire scan head can be immersed in a cleaning solution and the motor operated to move the cleaning solution through the various surfaces of the heat exchanger and around the rotor in order to clean it.

Signals processed by the electronics 430 in the scan head are transmitted to the display device 120 via a wired or wireless communication link (not shown).

As will be appreciated from the above disclosure, the scan head described above is able to dissipate greater amounts of heat due to the action of the motor drawing air that is used to remove the heat. Because the rotor of the motor is not electrically connected to the scan head it can removed from the scan head or the scan head can be immersed for cleaning purposes. Because the heat of the electronics in the scan head can be more effectively removed, greater integration of heat producing electronics can be incorporated into the scan head. In addition, more signal processing functions can be performed by the electronics without causing the scan head to overheat. This allows greater functionality to be provided in a small form factor ultrasound imaging machine thereby giving greater diagnostic capabilities to doctors, first responders and other medical personnel.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A scan head for an ultrasound imaging system, comprising:
   a scan head body;
   a number of transducer elements disposed within the scan head body;
   a number of electronic components that are electrically coupled to the transducer elements for driving the transducer elements and for processing received echo signals;
   wherein the electronic components are hermetically sealed within a thermally conductive compartment that is spaced from an interior surface of the scan head body to form a plenum between the thermally conductive compartment and the interior surface of the scan head body and wherein the scan head further includes
   a magnetically controlled fan having motor controlling electronics that are sealed within the thermally conductive compartment and a rotor with a number of fan blades configured to be moved by the motor controlling electronics in order to force air through the plenum and remove heat generated by the electronic components.

2. The scan head of claim 1, wherein the scan head is configured to be submersible in a cleaning fluid to allow the cleaning fluid to enter the space between the thermally conductive compartment and interior surface of the scan head body.

3. The scan head of claim 2, wherein the rotor is configured to be moved by the motor controlling electronics to move the cleaning fluid in order to clean the rotor.

* * * * *